US011592335B2

(12) United States Patent
Wang et al.

(10) Patent No.: US 11,592,335 B2
(45) Date of Patent: Feb. 28, 2023

(54) EAR THERMOMETER WITH A PROBE COVER EJECTION DEVICE

(71) Applicant: MICROLIFE CORPORATION, Taipei (TW)

(72) Inventors: Yi-Shun Wang, Taipei (TW); Chin-Chung Yu, Taipei (TW)

(73) Assignee: MICROLIFE CORPORATION, Taipei (TW)

( * ) Notice: Subject to any disclaimer, the term of this patent is extended or adjusted under 35 U.S.C. 154(b) by 329 days.

(21) Appl. No.: 17/069,903

(22) Filed: Oct. 14, 2020

(65) Prior Publication Data
US 2021/0108965 A1    Apr. 15, 2021

(30) Foreign Application Priority Data
Oct. 14, 2019    (CN) .......................... 201910974069.7

(51) Int. Cl.
*G01J 5/00*    (2022.01)
*G01J 5/02*    (2022.01)

(52) U.S. Cl.
CPC ............. *G01J 5/0011* (2013.01); *G01J 5/021* (2013.01)

(58) Field of Classification Search
CPC ........... G01J 5/0011; G01J 5/021; A61B 5/01; A61B 2562/00
USPC .......................................................... 702/136
See application file for complete search history.

(56) References Cited

U.S. PATENT DOCUMENTS

| 6,367,973 | B2 | 4/2002 | Yamaka |
| 6,786,636 | B1 | 9/2004 | Huang et al. |
| 7,494,273 | B2 | 2/2009 | Huang et al. |
| 8,517,603 | B2 * | 8/2013 | Fraden ................. G01J 5/08 374/208 |
| 9,464,940 | B2 | 10/2016 | Chen et al. |
| 2006/0120432 | A1 | 6/2006 | Lantz et al. |
| 2010/0260230 | A1 | 10/2010 | Lane et al. |

(Continued)

FOREIGN PATENT DOCUMENTS

| CN | 2636214 Y | 8/2004 |
| CN | 101140189 B | 12/2010 |

(Continued)

*Primary Examiner* — Gail Kaplan Verbitsky
(74) *Attorney, Agent, or Firm* — Juan Carlos A. Marquez; Marquez IP Law Office, PLLC

(57) ABSTRACT

The application provides an ear thermometer with a probe cover ejection device. The ear thermometer comprises a holding body and a measuring assembly disposed at one end of the holding body, which comprises a probe, a rotating member, and a socket. The rotating member includes a ring cover with an opening formed in a middle of the ring cover, at least one first abutting portion axially extended from a lateral side of the ring cover, and a lever portion radially extended from the lateral side of the ring cover. The socket includes a circular bottom surface and a closed section and an open section defined on a periphery of the circular bottom surface, a side wall surface vertically provided on the closed section, an accommodating space sandwiched between the side wall surface and the circular bottom surface, and at least one second abutting portion formed on the circular bottom surface. In this way, the dual motions of the radial and axial directions can be used to ensure that the probe cover can be reliably ejected and removed from the probe.

20 Claims, 18 Drawing Sheets

(56) References Cited

U.S. PATENT DOCUMENTS

| | | |
|---|---|---|
| 2012/0027047 A1 | 2/2012 | Lane et al. |
| 2013/0128926 A1 | 5/2013 | Fraden |
| 2013/0245488 A1* | 9/2013 | Quinn .................... G01J 5/021 |
| | | 600/549 |

FOREIGN PATENT DOCUMENTS

| | | |
|---|---|---|
| CN | 201767955 U | 3/2011 |
| CN | 104011522 A | 8/2014 |
| WO | 2010/078219 A1 | 7/2010 |

* cited by examiner

EAR THERMOMETER WITH A PROBE COVER EJECTION DEVICE

CROSS-REFERENCE TO RELATED APPLICATION

This application claims priority from China Patent Application No. 201910974069.7 filed on Oct. 14, 2019, which are hereby incorporated herein by reference in its entirety.

BACKGROUND OF THE INVENTION

1. Field of the Invention

The present invention relates to the field of an ear temperature measuring apparatus, in particular to an ear thermometer with a probe cover ejection device that uses both radial rotation and axial displacement to reliably eject the probe cover. Accordingly, the probe cover is facilitated to be replaced by a new one.

2. Description of Related Art

The human core temperature measurement tool has been developed from the early mercury-type axillary temperature, oral temperature or rectal temperature thermometers up to now. Infrared (IR) thermometers have become popular body temperature measurement products. The mercury thermometer is placed in the mouth, armpit or rectum of the human body so that the mercury within it expands and flows into the hollow tube in response to the temperature rise, and then the body temperature value is obtained by reading the scale mark corresponding to the expended mercury. However, mercury thermometers require a long waiting time for such measurement, and these measured parts of the body are also relatively difficult to measure for infants or elders. Furthermore, in hospitals or clinics, for example, body temperatures need to be quickly measured for various patients in line so that the mercury thermometers cannot be effectively applied to these situations or objects. Therefore, thermometer products utilizing infrared measurement technology have been widely used to measure the temperature of the human body quickly and accurately.

Infrared thermometers are generally divided into two types including ear thermometers and forehead thermometers. Ear thermometers are used to measure the eardrum temperature of the human body by extending into the ear canal, and forehead thermometers are used to measure the forehead temperature of the human body. In the case of ear thermometers, since the probe needs to be inserted into the ear canal during measurement, it will touch the surface of the ear canal. Therefore, at home or a medical place, multiple people must share the same thermometer so as to easily cause cross infection. In order to be free of such cross infection, it is necessary to prevent the probe from directly touching the ear canal of the subject through a corresponding probe cover provided outside the ear thermometer probe for each.

The probe cover is put on the probe before the measurement in practice, and then the probe is inserted into the ear canal. Afterward, the probe cover is taken off from the probe when the measurement is completed or the subject is to be changed. When removing the probe cover, if someone pull it down directly by hand, it is easy to damage the probe cover due to its structural characteristics, and even cause part of the probe cover to be left on the probe, and the other part is apart from the probe. Also, the broken probe cover cannot be used again. Generally speaking, especially for ward care, each inpatient will be provided with a probe cover for personal use so that nursing staff can enter the ward to measure body temperature regularly. If the probe covers are damaged every time they are disassembled, the considerable cost of consumables will be incurred when the body temperature measurement is conducted several times per day for nursing care. A similar problem is encountered even for personal household use. On the other hand, during a clinic or outpatient visit, medical staffs need to repeat actions such as putting on probe covers, measuring body temperature, and removing probe covers to proceed with the temperature measurement of each patient. Based on the various actual application of the above infrared ear thermometers, how to quickly and accurately remove the probe cover is a very important design point.

At present, there are some patent literatures that propose how to remove the probe covers on the ear thermometer. For example, the People's Republic of China Patent Publication No. CN2636214Y (corresponding to the US Patent Publication No. U.S. Pat. No. 6,786,636B1), and the People's Republic of China Patent Publication No. CN101140189B (corresponding U.S. Patent Publication No. U.S. Pat. No. 7,494,273B2), People's Republic of China Patent Publication No. CN104011522A, U.S. Patent Publication No. US2010/0260230A1, U.S. Patent Publication No. US2012/0027047A1, People's Republic of China Patent Publication No. CN201767955U, U.S. Patent Publication No. US2013/0128926A1, PCT Patent Publication No. WO2010/078219A1, US Patent Publication No. US2006/0120432A1, and US Patent Publication No. U.S. Pat. No. 6,367,973B2 and other literatures have disclosed related contents. The aforementioned patent literatures are all invented to push the probe cover outward only along an "axial direction" and then remove it from the probe through various pushing structure designs on the ear thermometers. However, it would be noted that in order to only prevent the probe from contacting the skin of the ear canal of the subject without affecting infrared detection, the structure of the probe cover is generally thin and soft at its front end and thick and hard at its bottom end. Therefore, the existing axial pushing techniques actually raise the problem of difficult detachment of the probe cover, or only deform the probe cover but cannot completely push it away from the probe. In this regard, there is great room for improvement.

There may be some techniques that do not use a pushing portion to move a probe cover outwards. For example, the US Patent Publication No. U.S. Pat. No. 9,464,940B2 just changes the position of the probe to make the probe cover apart. This application takes a different way from those used in the foregoing patent literatures that directly and axially push the probe cover apart by a means of pulling a lever, and however, it still has the movement of axially pushing the probe cover apart from the probe. Thus, there are the same disadvantages above for this prior application.

In view of this, the inventor of the present invention conceives and proposes an ear thermometer with a probe cover ejection device to effectively overcome or solve the various disadvantages and problems of the part of the ear thermometer for disengaging the probe cover.

SUMMARY OF THE INVENTION

According to one aspect of the application, an ear thermometer with a probe cover ejection device is provided to utilize a specially designed measuring assembly to make a probe cover be simultaneously exerted by a radial rotation force and an axial displacement force. Then, the probe cover can be removed from the ear thermometer, and has an excellent removal effect.

In view of the foregoing aspect, in one embodiment, the present application provides an ear thermometer with a probe cover ejection device, comprising: a holding body; and a measuring assembly disposed at one end of the holding body and comprising: a probe; a rotating member including a ring cover with an opening formed in a middle of the ring cover, at least one first abutting portion axially extended from a lateral side of the ring cover, and a lever portion radially extended from the lateral side of the ring cover; and a socket including a circular bottom surface and a closed section and an open section defined on a periphery of the circular bottom surface, a side wall surface vertically provided on the closed section, an accommodating space sandwiched between the side wall surface and the circular bottom surface, and at least one second abutting portion formed on the circular bottom surface; wherein the rotating member is placed in the accommodating space, and the first abutting portion is pressed against the second abutting portion to be in a relatively slidable state, the lever portion is protruded at a position of the open section of the socket, and the probe passes through the opening and one end of the probe is fixed to the circular bottom surface of the socket; wherein when the lever portion is displaced within the open section under force, the first abutting portion moves relative to the second abutting portion so that the rotating member whole and synchronously rotate radially and move axially to make a probe cover sheltered on the probe be radially and axially pushed and displaced simultaneously, whereby a force-exerted area or region of the pushed and displaced probe cover is increased during a removal of the probe cover through the foregoing structures and movements so as to effectively prevent incomplete detachment or breakage caused by only axially pushing and displacing the probe cover as the prior applications, and thus the probe cover can be reliably removed.

Preferably, the first abutting portion is an inclined surface and has a first valley and a first peak oppositely disposed so that the first abutting portion relatively abuts against the second abutting portion at a position that moves from the first valley to the first peak when the lever portion is displaced in the open section, wherein the first abutting portion is a plane or a curved surface.

Preferably, the second abutting portion is an inclined surface and has a second valley and a second peak oppositely disposed so that the second abutting portion relatively abuts against the first abutting portion at a position the moves from the second valley to the second peak when the lever portion is displaced in the open section, wherein the second abutting portion is a plane or a curved surface.

Preferably, the ear thermometer further comprises a spring, and a ring rib is protruded from the opening of the ring cover. One end of the spring abuts against the ring rib, and the other end of the spring abuts against a retaining surface of the probe so that the lever portion of the rotating member is given with an automatic restoration function.

Preferably, the other side of the ring cover opposite to the first abutting portion is axially extended to form a plurality of convexes so as to increase pushing force relatively applied by the rotating member to the probe cover.

Preferably, the number of the at least one second abutting portion is three, and the three second abutting portions are arranged equidistantly along a circumference of the circular bottom surface; further, the number of the at least one first abutting portion is three, and the three first abutting portions are respectively corresponding to and abutted against the three second abutting portions so that a relative motion between the rotating member and the socket can be more stable. A distributed force applied to the probe cover is also more even.

Preferably, the circular bottom surface of the socket has a pair of aligned protrusions, and one end of the probe has a pair of aligned grooves corresponding to the aligned protrusion so that the aligned protrusions are located in the aligned grooves when the probe is fixed to the socket, whereby the precision of the assembled probe can be improved, and positioning and foolproof effects can be achieved.

In view of above, the ear thermometer with the probe cover ejection device proposed by the present application utilizes a special structure design so that the whole rotating member simultaneously rotate radially and move axially when the rotating member is motioned. The probe cover can be quickly and reliably ejected and removed from the probe by simultaneously exerting a radial rotation force and a pushing-outward displacement force on the probe cover. Through the second abutting portion on the circular bottom surface of the socket and the first abutting portion of the rotating member, the rotating member can simultaneously be radially rotated and axially displaced in response to an interactive motion between the first abutting portion and the second abutting portion after the lever portion is displaced by applied force. Accordingly, compared with a conventional ear thermometer, the area of the probe cover to which the force is applied can be extended from points to a surface so that the exact removal of the probe cover can be greatly improved and the integrity of the probe cover can be better maintained after removal to facilitate reuse.

BRIEF DESCRIPTION OF THE DRAWINGS

In order to sufficiently understand the essence, advantages and the preferred embodiments of the present invention, the following detailed description will be more clearly understood by referring to the accompanying drawings.

DETAILED DESCRIPTION OF THE INVENTION

Figure 1A:
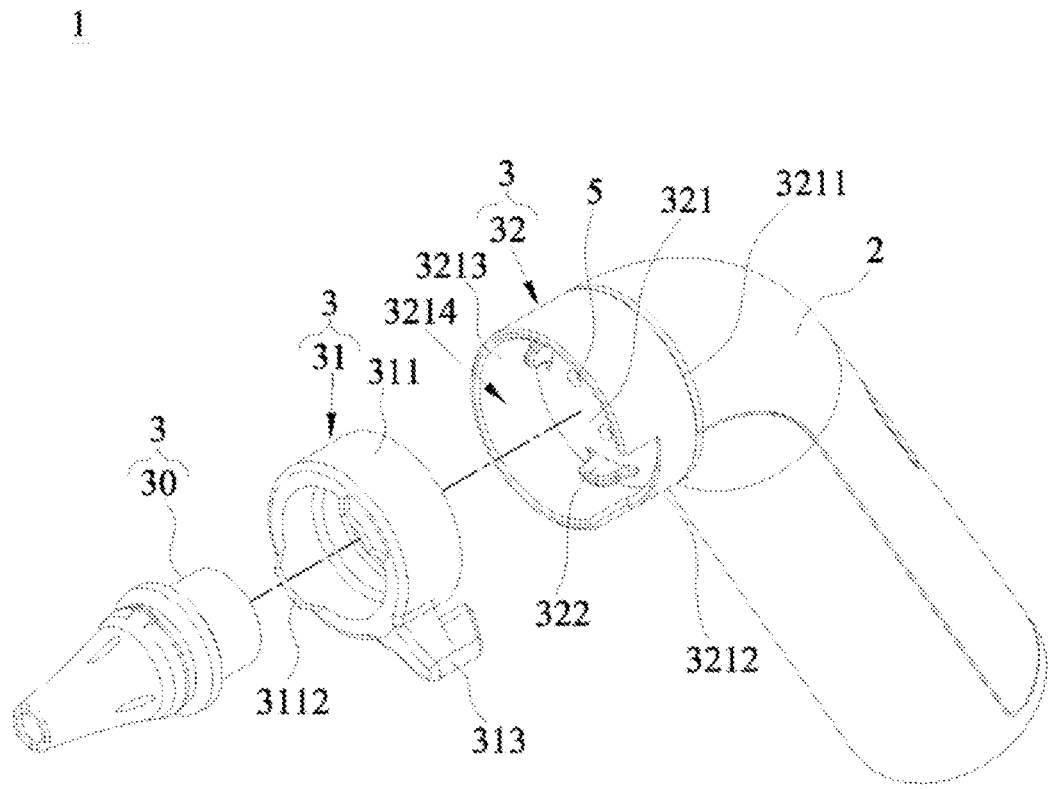
FIG. 1A is an exploded perspective schematic diagram (1) of the ear thermometer according to the first embodied model of the preferred embodiment of the present application.
Figure 1B:
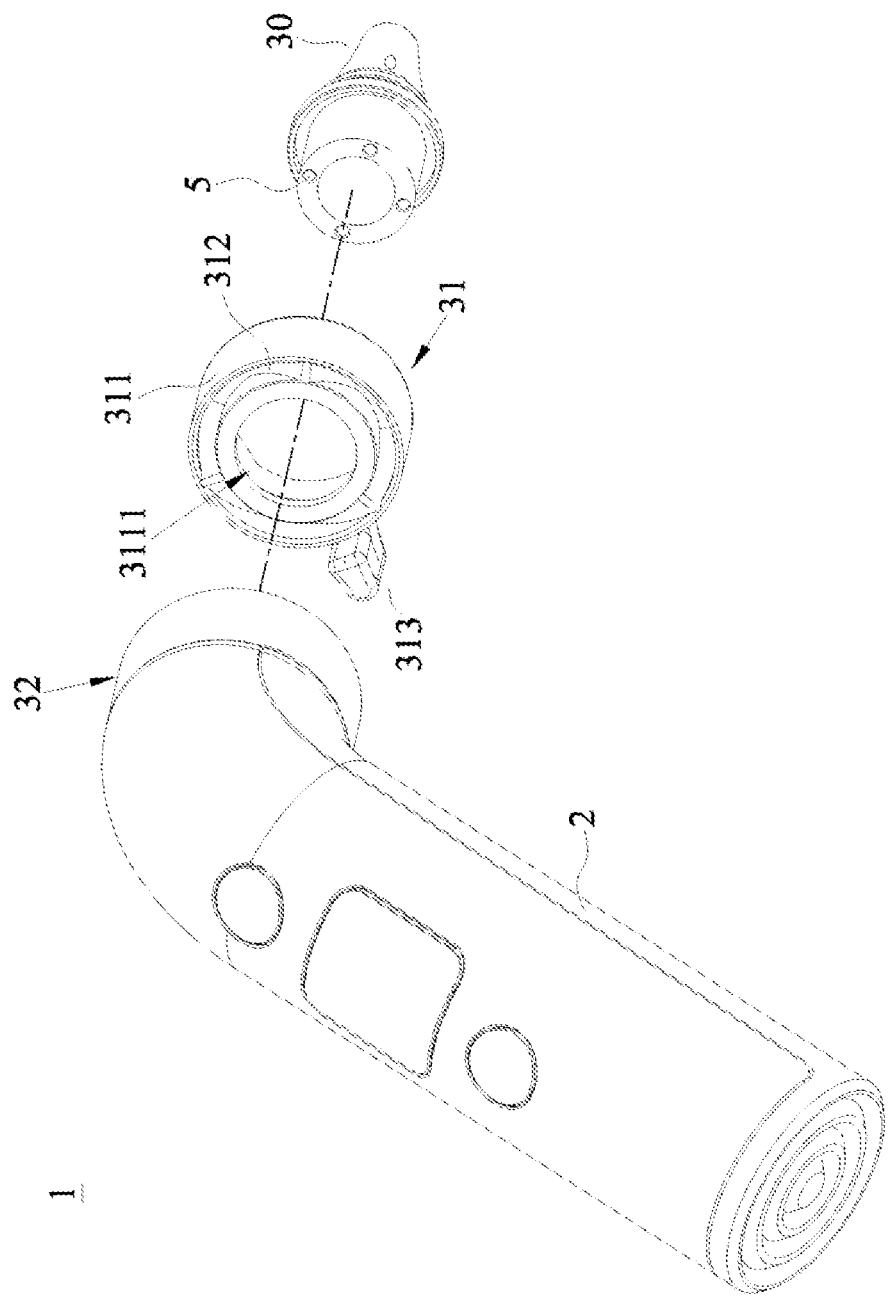
FIG. 1B is an exploded perspective schematic diagram (2) of the ear thermometer according to the first embodied model of the preferred embodiment of the present application.

The following description shows the preferred embodiments of the present invention. The present invention is described below by referring to the embodiments and the figures. Thus, the present invention is not intended to be limited to the embodiments shown, but is to be accorded the principles disclosed herein. Furthermore, that various modifications or changes in light thereof will be suggested to persons skilled in the art and are to be included within the spirit and purview of this application and scope of the appended claims.

Referring to FIGS. 1 to 3F, these figures respectively show exploded perspective schematic diagram of each ear thermometer in the first embodied model of the preferred embodiment of the present invention, a partially cross-sectional schematic diagram of the measuring assembly covered with a probe cover, and a schematic diagram of each application. As shown in the figures, the present application discloses an ear thermometer 1 with a probe cover ejection device 39, which comprises a holding body 2 and a measuring assembly 3. The holding body 2 is for the user to hold, and contains a control circuit and a power supply (not shown). The measuring assembly 3 is disposed at one end of the holding body 2 and includes a probe 30 and the probe cover ejection device 39. The probe cover ejection device 39 includes a rotating member 31 and a socket 32. The ear thermometer 1 is a temperature measuring apparatus that uses infrared sensing principles. During measurement, the user grasps the holding body 2 and let the probe 30 reach into his ear canal to measure a body temperature through an infrared sensor. Also as mentioned above, in actual applications, a probe cover 4 will be put on the probe 30 during measurement as an isolating part to avoid cross infection in order to facilitate the use of the ear thermometer 1 for multiple people. After the body temperature is measured, the probe cover 4 can be ejected and removed by the measuring assembly 3. The structure of the ear thermometer 1 of the present application will be further described below.

The probe 30 contains a copper cap, an infrared sensing device and a copper sleeve (not shown in the figure). The foregoing copper cap, infrared sensing device and copper sleeve are assembled in sequence.

The rotating member 31 has a ring cover 311 and an opening 3111 is formed in the middle of the ring cover portion 311. A lateral side of the ring cover portion 311 axially extends to form at least one first abutting portion 312. A lever portion 313 is formed on the lateral side of the ring cover 311 along a radial direction. The socket 32 has a circular bottom surface 321 and defines a closed section 3211 and an open section 3212 on the periphery of the circular bottom surface 321. The closed section 3211 is perpendicularly provided with a side wall surface 3213, the side wall surface 3213 and the circular bottom surface 321 sandwich an accommodating space 3214, and at least one second abutting portion 322 is formed on the circular bottom surface 321. In these regards, the rotating member 31 is placed in the accommodating space 3214, the first abutting portion 312 is pressed against the second abutting portion 322 to be in a relatively slidable state, and the lever portion 313 is protruded at the position of the open section 3212 of the socket 32, and the probe 30 passes through the opening 3111 and its one end is fixed to the circular bottom surface 321 of the socket 32. When the lever portion 313 is displaced within the open section 3212 under force, the first abutting portion 312 moves relative to the second abutting portion 322 so that the rotating member 31 whole and synchronously rotate radially and move axially. Accordingly, when the user pulls the lever portion 313 to displace it within the open section 3212, through the radial rotation and axial displacement of the rotating member 31, the rotating member 31 exerts duel pushing and shifting forces in relative to the probe cover 4, and greatly increases the pushing and shifting area and stress applied by the rotating member 31 on the probe cover 4 so that the probe cover 4 can be reliably ejected outwards to achieve the removal result. It is also worth to note that, through the special structural design of the present application, the rotating member 31 will rotate radially and move axially at the same time when it is motioned, instead of only simple rotation.

Figure 2:
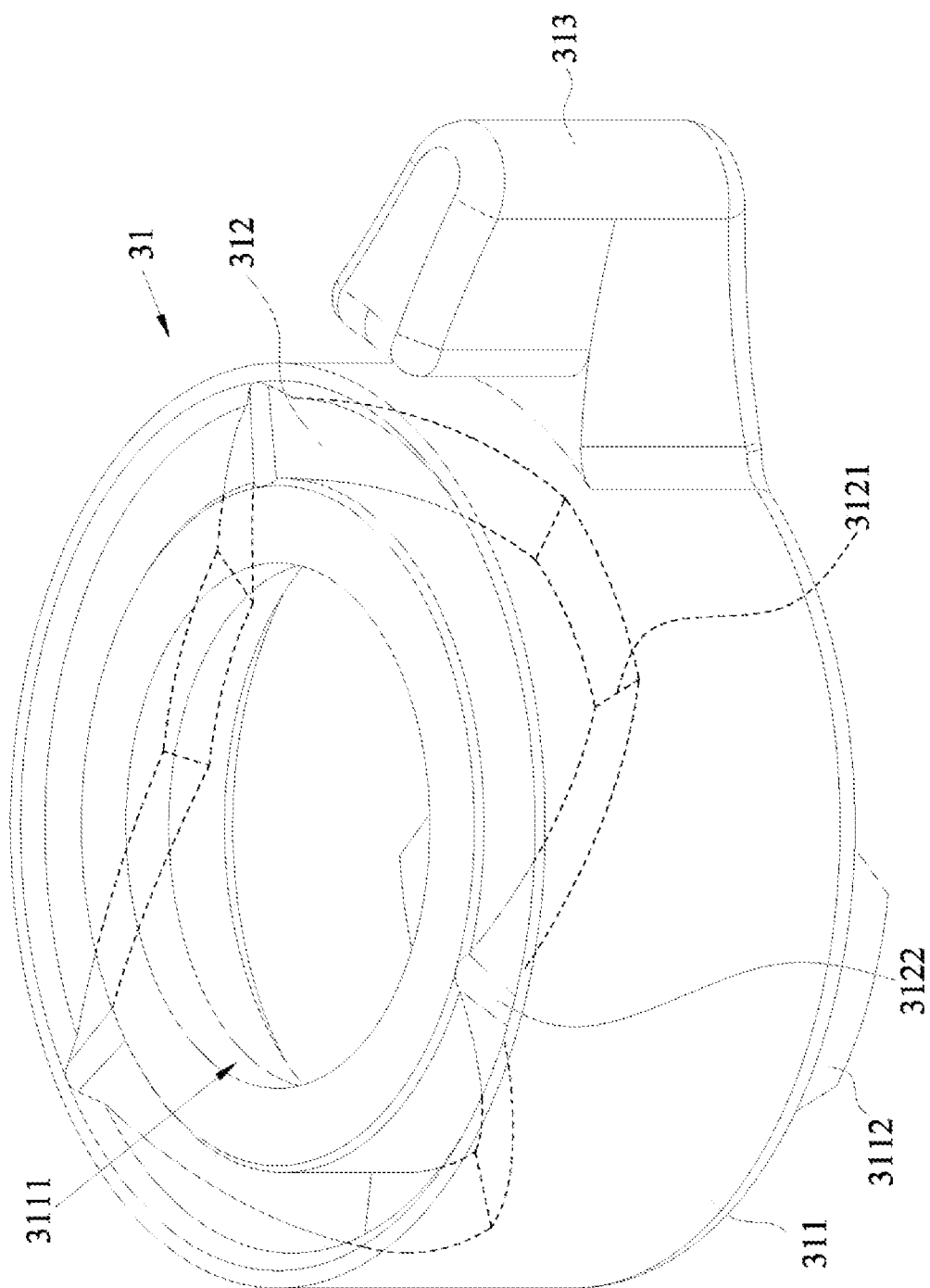
FIG. 2 is a schematic diagram of the structure of the rotating member according to the first embodied model of the preferred embodiment of the present application.
Figure 3A:
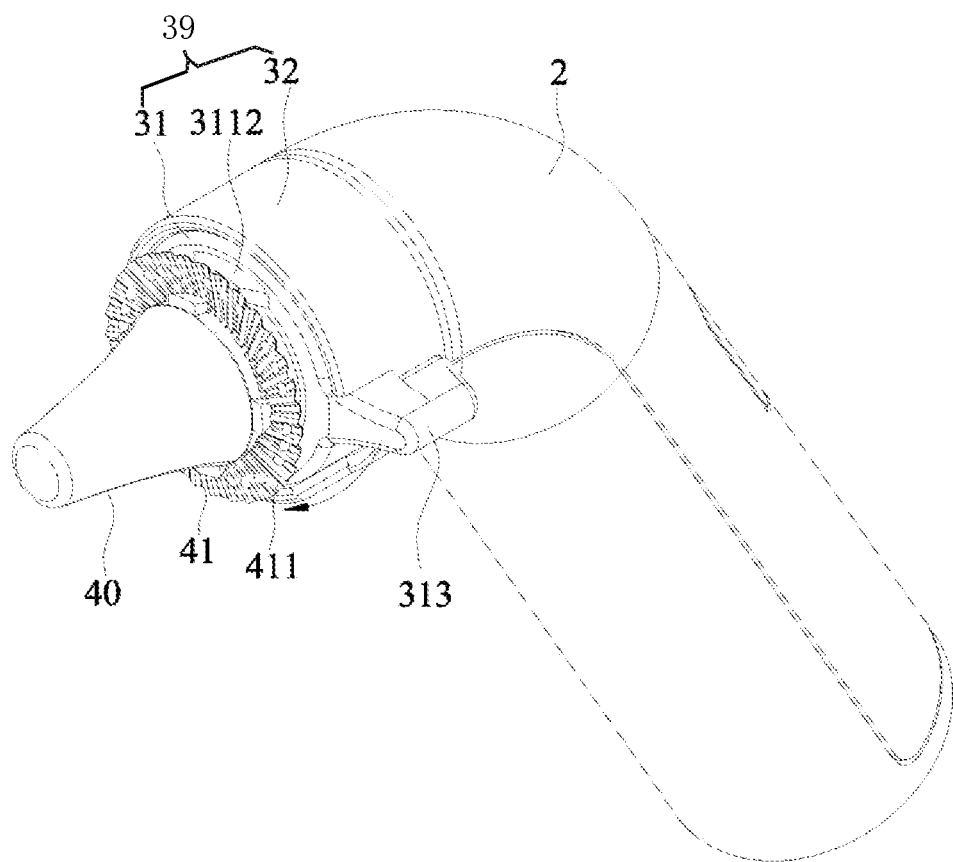
FIG. 3A is a schematic diagram of the application of the ear thermometer according to the first embodied model of the preferred embodiment of the present application.
Figure 3B:
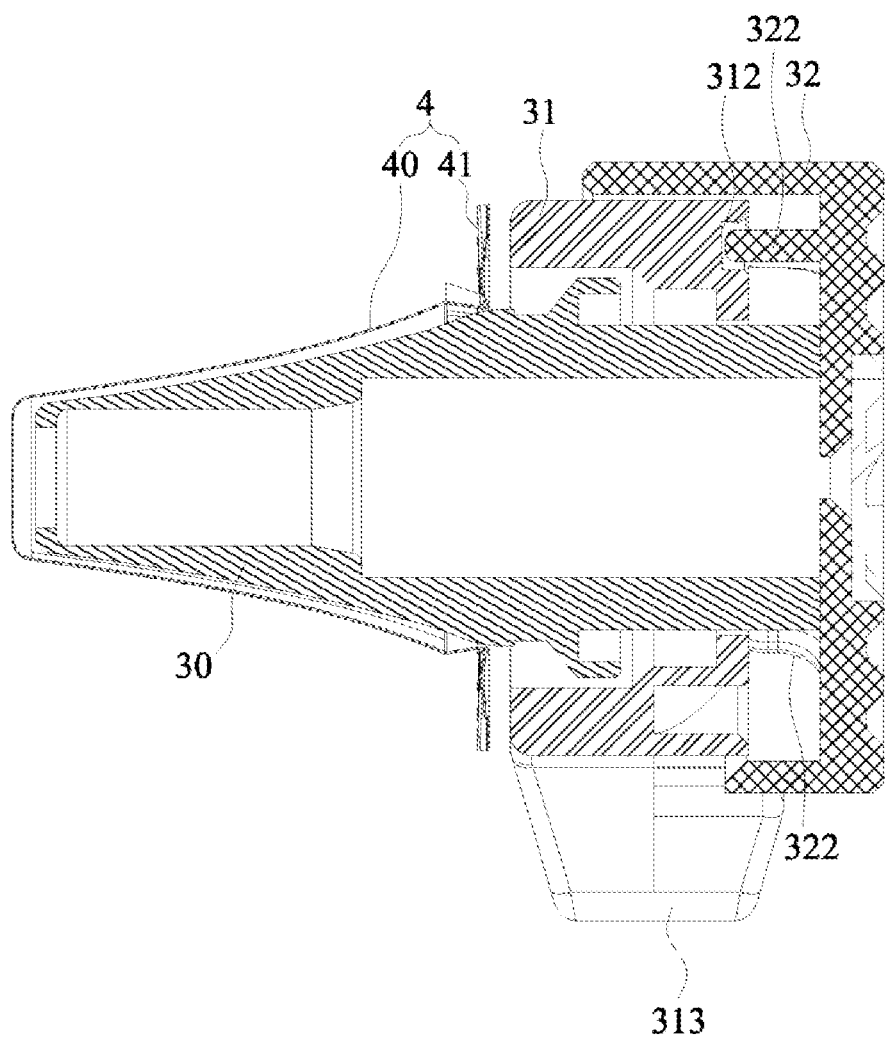
FIG. 3B is a partially cross-sectional schematic diagram of the measuring assembly covered with a probe cover according to the first embodied model of the preferred embodiment of the present application.
Figure 3C:
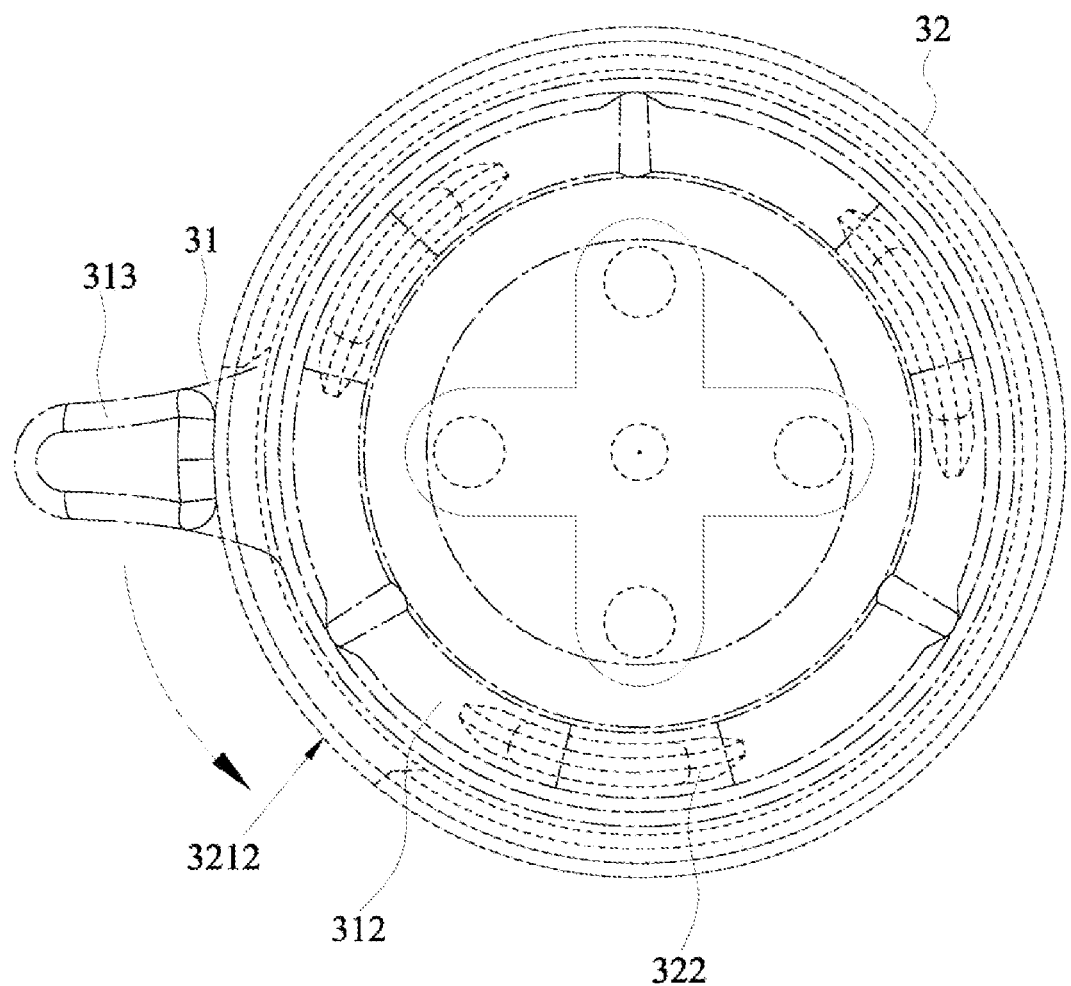
FIG. 3C is an exploded plane schematic diagram (1) of the ear thermometer according to the first embodied model of the preferred embodiment of the present application.
Figure 3D:
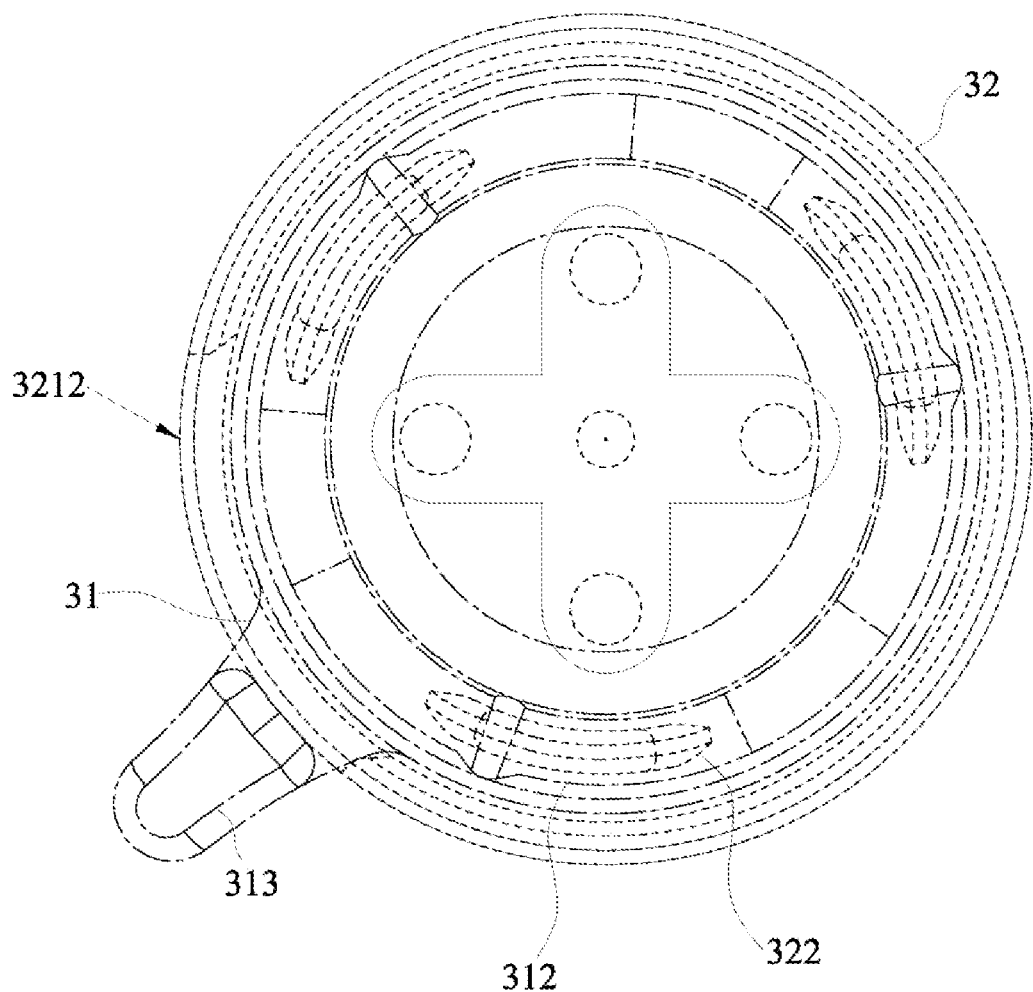
FIG. 3D is an exploded plane schematic diagram (2) of the ear thermometer according to the first embodied model of the preferred embodiment of the present application.
Figure 3E:
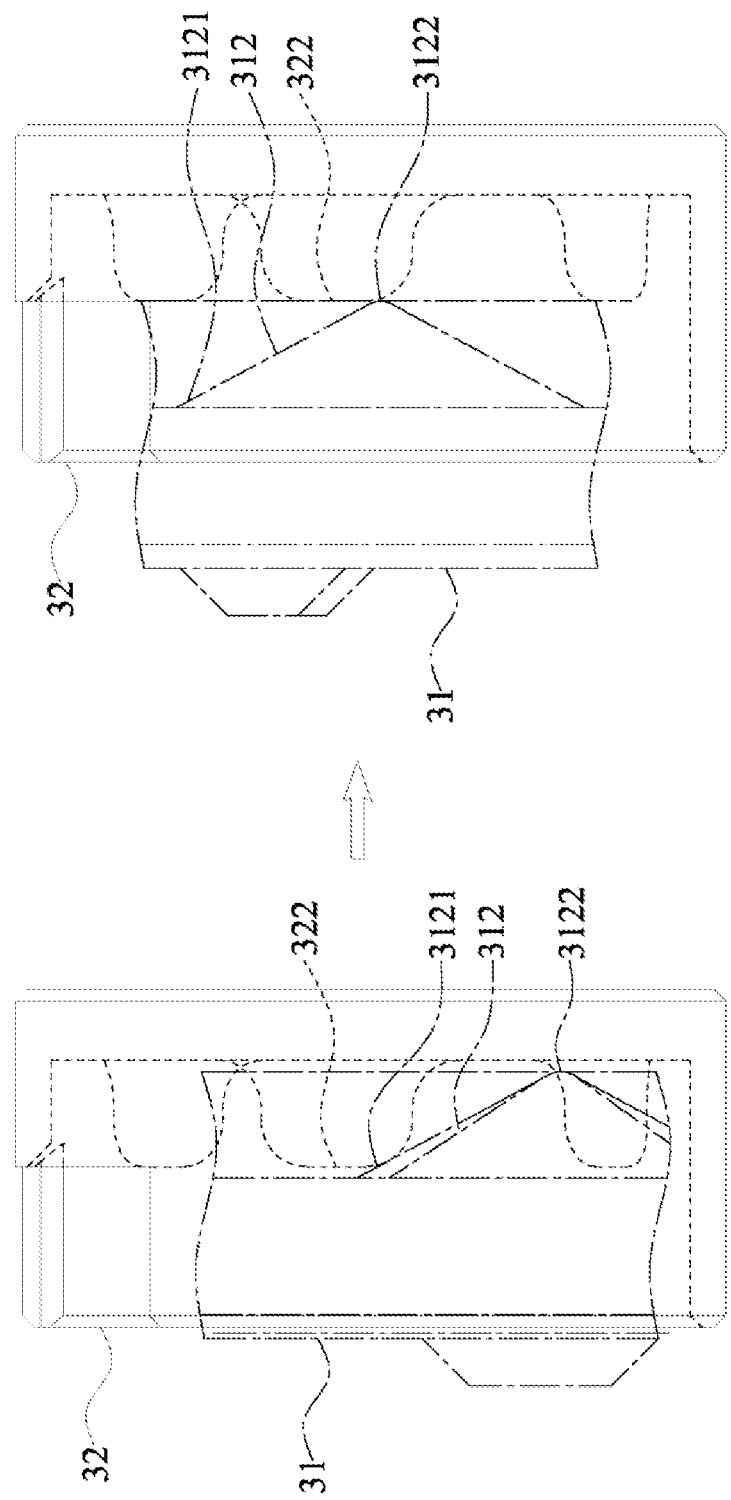
FIG. 3E is a schematic diagram of the lateral motion of the rotating member and the socket according to the first embodied model of the preferred embodiment of the present application.

The foregoing open section 3212 refers to the region where the lever part 313 is allowed to move, and the region may be a free space, or there is a small side wall extending slightly upward from the periphery of the circular bottom surface 321. In order to enable the first abutting portion 312 to slide in relative to the second abutting portion 322, in a practical design, the first abutting portion 312 may be an inclined surface or the second abutting portion 322 may be an inclined surface. In this regard, the rotating member 31 simultaneously has the radial rotation and axial displacement when the lever portion 313 moves in the open section 3212. Just one of the first abutting portion 312 and the second abutting portion 322 is formed as an inclined surface and it is enough to achieve the aforementioned results. The following is an example of the first abutting portion 312 being an inclined surface. If the first abutting portion 312 is an inclined surface, the first abutting portion 312 has a first valley 3121 and a first peak 3122 oppositely disposed so that the first abutting portion 312 relatively abuts against the second abutting portion 322 at a position that moves from the first valley 3121 to the first peak 3122 when the lever portion 313 is displaced in the open section 3212. Furthermore, the first abutting portion 312 may be a plane or a curved surface, and if the first abutting portion 312 is an obliquely curved surface, the first abutting portion 312 may be an obliquely curved concave surface or an obliquely curved convex surface. Referring to FIGS. 2 and 3E, it can be seen that the first abutting portion 312 is an inclined surface, and has the first valley 3121 and the first peak 3122. When the lever portion 313 is pushed, the first abutting portion 312 rotates radially as the lever portion 313 moves. Accordingly, the position of the first abutting portion 311 abutting against the second abutting portion 322 moves from the first valley 3121 to the first peak 3122. When the lever portion 313 of the rotating member 31 moves within the open section 3212, the rotating member 31 is enable to have simultaneous radial rotation and axial displacement due to the relative sliding motions between the first abutting portion 312 and the second abutting portion 322. Thus, the probe cover 4 is pushed away.

In addition, the other side of the ring cover 311 opposite to the first abutting portion 312 is axially extended to form a plurality of convexes 3112 so as to increase the pushing and shifting forces relatively applied by the rotating member 31 to the probe cover 4 through the convexes 3112. For example, in this embodiment, there are two convexes 3112 extended from the ring cover 311, and they are symmetrically arranged so that the distributed force applied to the probe cover 4 is more even when it is moved. The foregoing convexes 3112 can preferably be a structure with a cross-section somewhat like a trapezoid so as to have a better contact and force state for relatively abutting against the probe cover 4.

The number of the at least one second abutting portion 322 can be plural so that the rotating member 31 have a more stable radial rotation and axial displacement state when it and the socket 32 slide to each other. For example, there are three second abutting portions 322, and they are arranged equidistantly along the circumference of the circular bottom surface 321. Moreover, the number of the first abutting portion 321 can also be plural. For example, there are three first abutting portions 321, and the three first abutting portions 321 are respectively corresponding to and abutted against the three second abutting portions 311 upon their numbers and positions. Thus, through the three second abutting portions 322 respectively corresponding to the three first abutting portions 312, the rotating member 31 is more stable and can apply greater pushing and shifting force relatively to the probe cover 4 in response to the motion of the lever portion 313. Preferably, the three second abutting portions 322 are arranged with a three-point equidistant concept to have stable applied pushing force, which can have excellent results on both cost considerations and the magnitude of applied force.

Regarding the installation of the probe 30, the probe 30 of the ear thermometer 1 passes through one end of the opening 3111 and is mounted on the circular bottom surface 321 of the socket 32. Specifically, the probe 30 can be fixed to the circular bottom surface 321 by bonding or assembling each other by screws. That is, one end of the probe 30 and the circular bottom surface 321 can be provided with a plurality of screw holes 5. After the probe 30 passes through the opening 3111 and is fixed to the circular bottom surface 321, the screw holes 5 are aligned with each other, and then the probe 30 and circular bottom surface 321 are locked and fixed with screws to complete the assembly. For example, as shown in the figure, the circular bottom surface 321 has there are four screw holes 5, and the screw holes 5 are arranged in an equidistant ring shape. Further, the screw holes 5 are provided on the probe 30 according to the screw holes 5 of the circular bottom surface 321.

Regarding the detailed structure of the ear thermometer 1, as described above, the probe 30 of the ear thermometer 1 contains a copper cap, an infrared sensing device and a copper sleeve (not shown in the figure) to receive external infrared rays for the temperature measurement. The holding body 2 can be equipped with a control circuit with a processor, a control switch, and a power supply for starting and operating the ear thermometer. The processor may be a microprocessor (MCU), and is electrically connected to the infrared sensing device to perform the operation of programs, signal processing, and so on. The control switch is electrically connected to the circuit configuration for the user to turn on or off the ear thermometer and perform the temperature measurement. In order to let the infrared sensing device be electrically connected to the processor, the circular bottom surface 321 may be provided with a through hole 3216 for required electrical connecting devices to pass through. Furthermore, the holding body 2 may also be provided with a display screen to inform the user of the body temperature status or other information through visual presentation ways such as images and texts. The foregoing devices are already related to ones existing in the relevant technical fields, and will not be further discussed here. To preferably describe the main technical features of the present application, the foregoing infrared sensing device, wires and other device are not shown in FIG. 2.

In particular, the probe cover 4 for use with the ear thermometer 1 has a main structure similar to the probe 30, and has a sheathing portion 40 and a skirt portion 41. In consideration of the structural strength of the probe cover 4, the skirt portion 41 is provided with a plurality of bending stripes 411, and the bending stripes 411 are inclined and bent in the same direction. The measuring assembly 3 can correspondingly make the rotation direction of the rotating member 31 in response to the lever portion 313 be opposite to the bending direction of the bending stripes 411. Accordingly, when the probe cover 4 is pushed and ejected outwards by the rotating member 31, it can have a strong disengaged force due to the reverse pushing so that the probe cover 4 can be reliably removed. In other embodiments, a plurality of ribs may be provided in the sheathing portion 40 so that a thermal insulating room can be formed between the eardrum and the probe 30 when the probe cover 4 covers the probe 30.

Figure 3F:
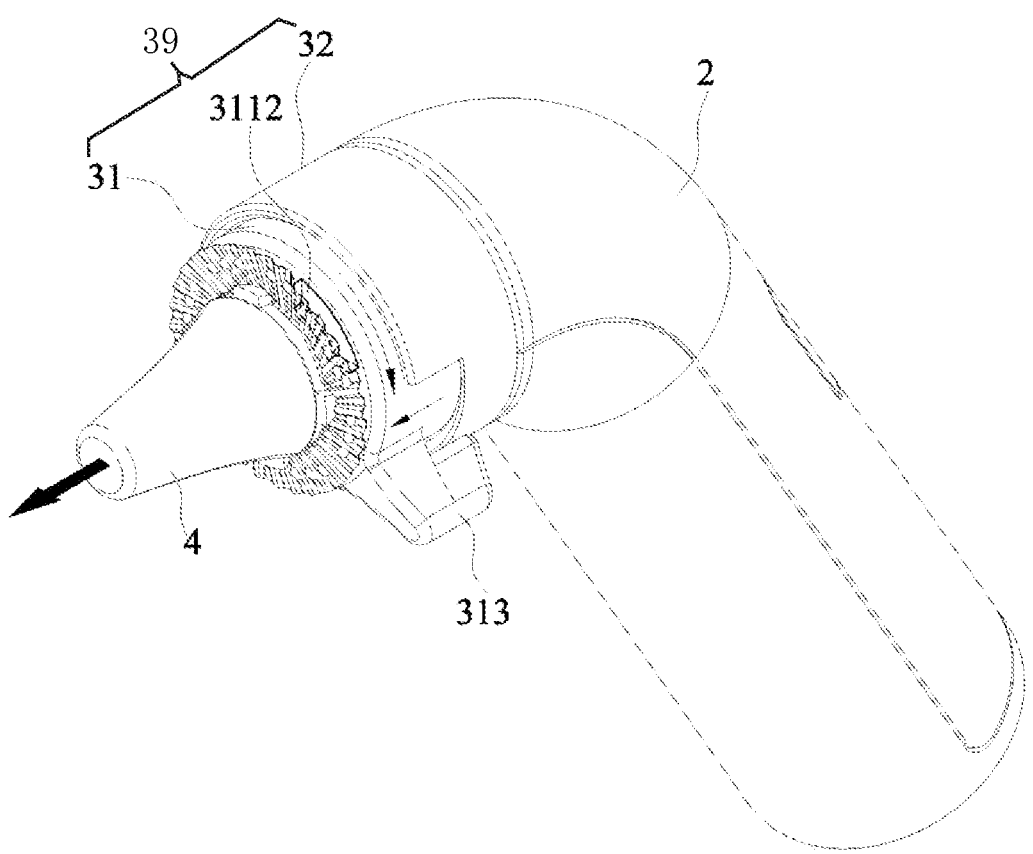
FIG. 3F is a perspective schematic diagram of the application of the ear thermometer according to the first embodied model of the preferred embodiment of the present application.

Referring to FIGS. 2 and 3A to 3F, the probe cover 4 covers the probe 30 for facilitating the temperature measurement during an operation. When the probe cover 4 is to be removed, the lever portion 313 is pulled under force to displace in the open section 3212 so that each of the first abutting portions 312 of the rotating member 31 slides against the corresponding one of the second abutting portions 322. Accordingly, the first abutting portion 312 relatively abuts against the second abutting portion 322 at a position that moves from the first valley 3121 to the first peak 3122. In the meanwhile, the whole rotating member 31 will have both radial rotation and axial displacement (as shown in FIG. 3F), and then the probe cover 4 is push outward and apart from the probe 30. It is reiterated here that by mating the rotating member 31 to the socket 32, the applied force and area on the pushed probe cover 4 can be greatly increased in response to the radial rotation and axial displacement of the rotating member 31 so that the probe cover 4 can be reliably ejected and removed and also can be prevented from deformation. When the probe cover 4 is removed next time, the user pulls the lever portion 313 again to force it to move within the open section 3212, and the first abutting portions 312 correspondingly slide on the second abutting portions 322 so that the rotating member 31 rotates radially and moves axially simultaneously, and the probe cover 4 can be ejected and removed.

Figure 4:
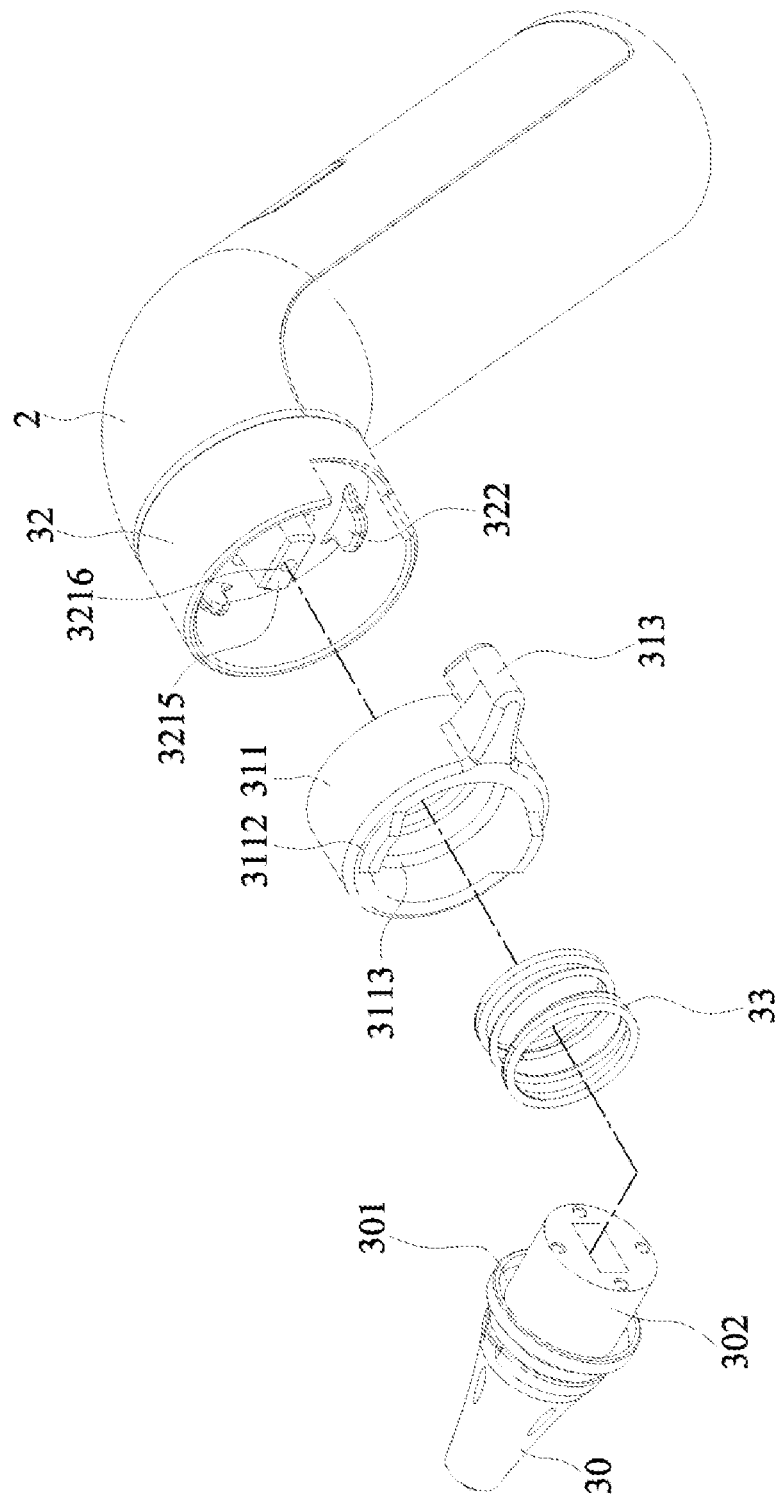
FIG. 4 is an exploded perspective schematic diagram of the ear thermometer according to the second embodied model of the preferred embodiment of the present application.
Figure 5:
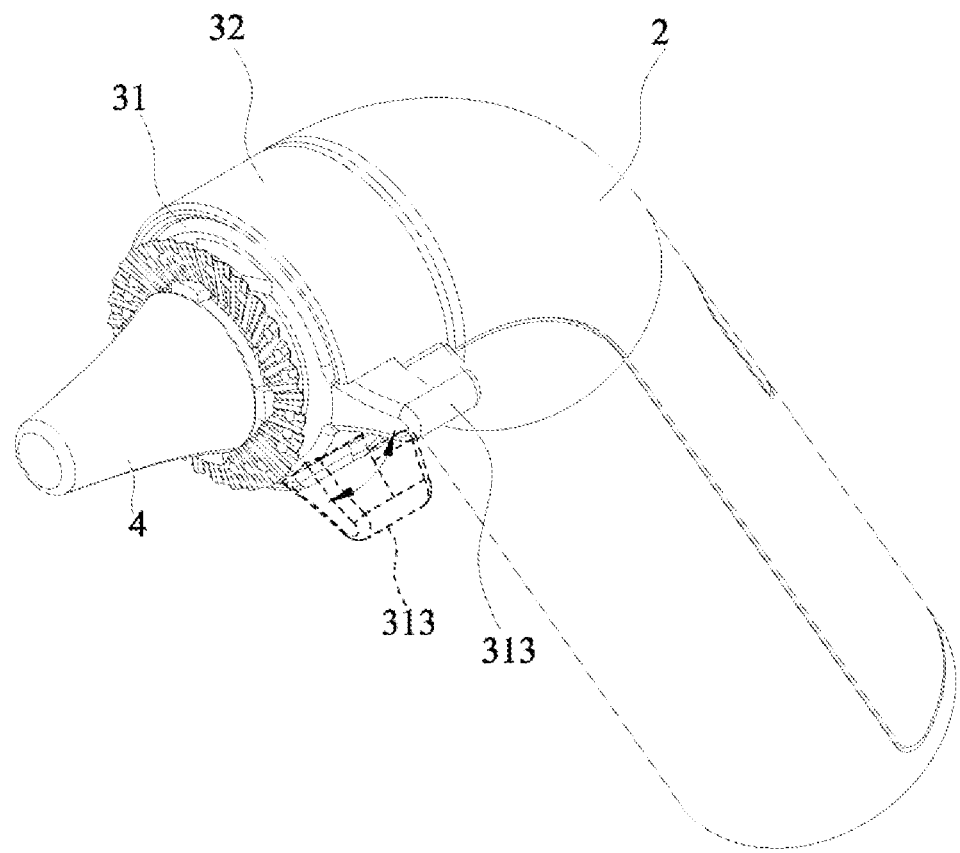
FIG. 5 is a schematic diagram of the ear thermometer according to the second embodied model according to the preferred embodiment of the present application.
Figure 6A:
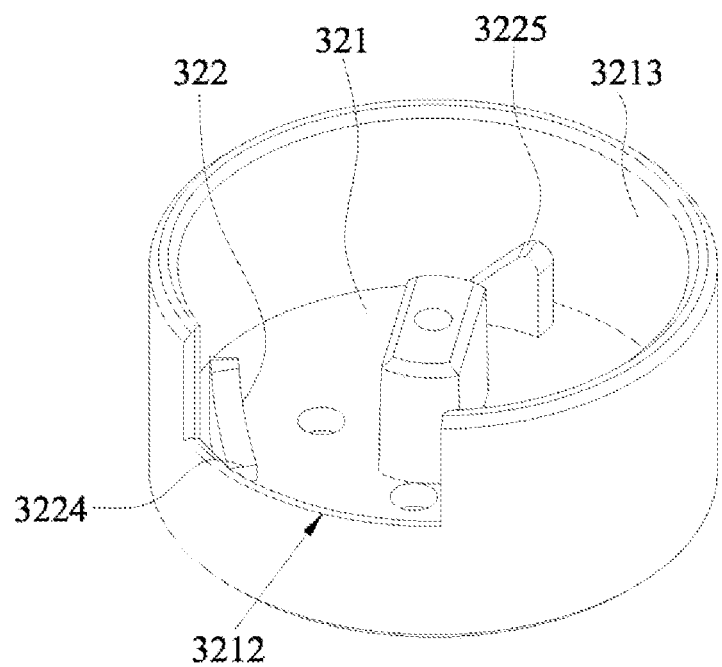
FIG. 6A is a schematic diagram of an embodied model of the socket according to the preferred embodiment of the present application.
Figure 6B:
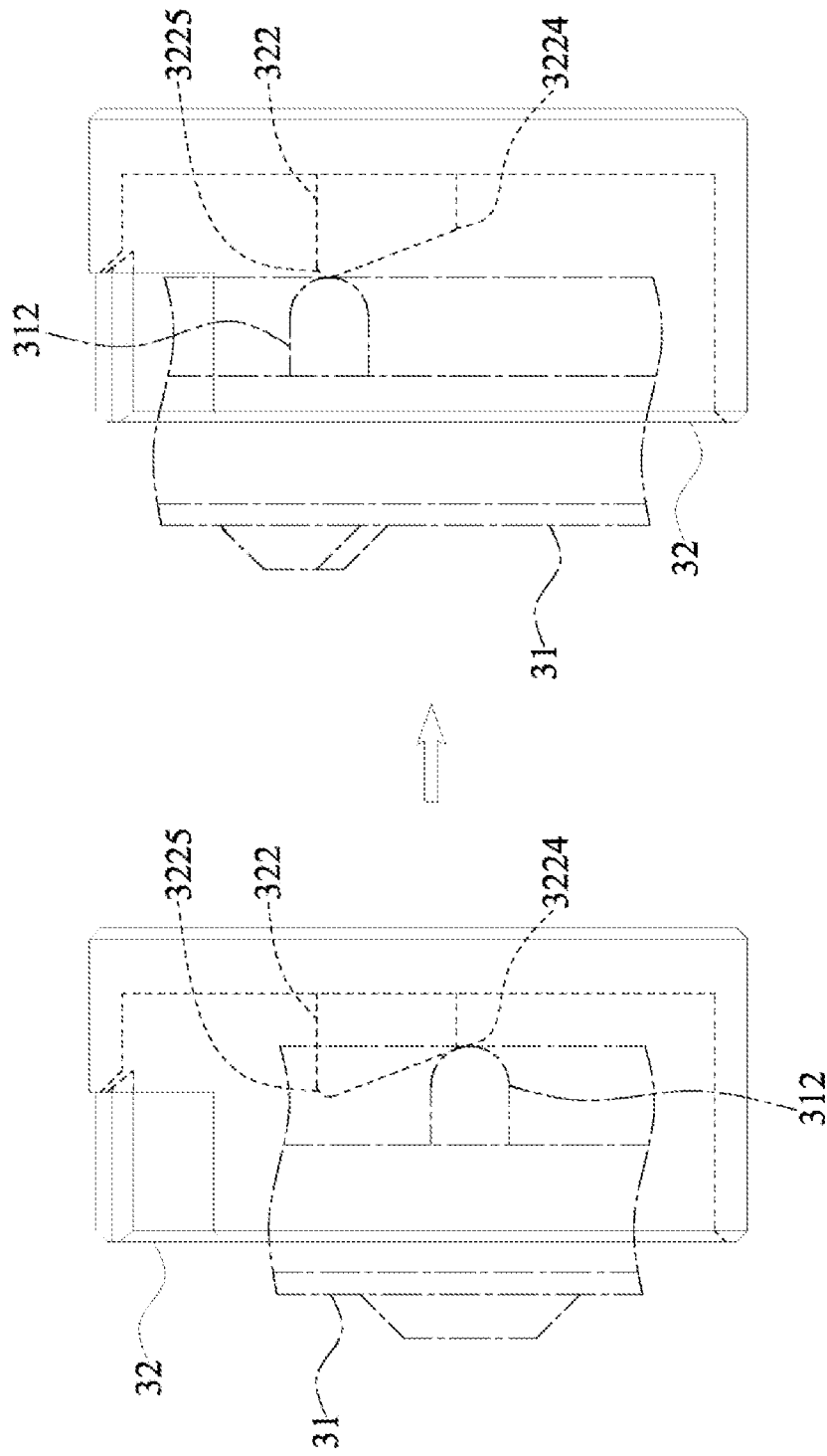
FIG. 6B is a schematic diagram of the lateral motion of the rotating member and the socket according to the embodied model of the preferred embodiment of the present application.

Further referring to FIGS. 4 and 5, they show exploded and assembled perspective schematic diagrams of the ear thermometer according to the second embodied model of the present application. In order to improve the convenience of use and the accuracy of restoration, the ear thermometer 1 is further equipped with a spring 33, and a ring rib 3113 is protruded from the opening 3111 of the ring cover 311. One end of the spring 33 abuts against the ring rib 3113, and the other end of the spring 33 abuts against the retaining surface 301 of the probe 30. The spring 33 exerts an elastic force to the rotating member 31 for automatic restoration, which greatly improves the convenience in use. When the first abutting portion 312 relatively abuts against the second abutting portion 322 at a position that moves from the first valley 3121 to the first peak 3122, the spring 33 is compressed. When the lever portion 313 is released to let the spring 33 be free of compression and generate a reverse elastic force, the rotating member 31 can quickly and surely move in the reverse direction due to the elastic force of the spring 33 so that the rotating member 31 is axially displaced towards the socket 32 for restoration.

In order to enhance the combined strength of the socket 32 and the probe 30 and to improve the alignment precision during assembly, the circular bottom surface 321 of the socket 32 has a pair of aligned protrusions 3215, and one end of the probe 30 has a pair of aligned grooves 302 corresponding to the aligned protrusion 3215. In this regard, when the probe 30 is fixed to the socket 32, the aligned protrusion 3215 is located in the aligned groove 302. As mentioned in the previous paragraph, the socket 32 and the probe 30 can be combined by bonding or screw locking. However, no matter which combination way is taken, the structures of the aligned protrusion 3215 and the aligned groove 302 can make the assembly of them more convenient, and achieve the effect of positioning foolproof. After the two parts are assembled and fixed with each other, the aligned protrusion 3215 is located in the aligned groove 302 so as to prevent the probe 30 from loosening or skewing. Consequently, the assembly of the probe 30 and the socket 32 is more firm.

Further referring to FIGS. 6-9B, there figures show schematic diagrams of other structural models of the socket 32 according to the preferred embodiment of the present application. Preferably, as shown in FIGS. 6A and 6B and described above, the second abutting portion 332 is an inclined surface and has a second valley 3224 and a second peak 3225 oppositely disposed so that the first abutting portion 312 relatively abuts against the second abutting portion 322 at a position the moves from the second valley 3224 to the second peak 3225 when the lever portion 313 is displaced in the open section 3212. Accordingly, the rotating member 31 simultaneously has radial rotation and axial displacement in response to this relative sliding motion, and then the probe cover 4 can be removed. Similarly, if the second abutting portion 322 is an inclined surface, it can be a planar structure or a curved surface structure. When the second abutting portion 322 is a curved surface structure, it can be a curved convex surface or a curved concave surface. If the second abutting portion 322 is an inclined surface, the first abutting portion 312 may be designed as a bump for abutting against the second abutting portion 322. The second abutting portion 322 may or may not have an inclined surface, and it just needs to meet the requirement that the first abutting portion 312 and the second abutting portion 322 can slide relatively. As shown in FIGS. 6A and 6B, if the second abutting portion 322 is an inclined surface, when the lever portion 313 is forced to move in the opening section 3212, the first abutting portion 312 abuts against the second abutting portion 322 and moves. In other words, if the second abutting portion 322 is formed as such a configuration, when the lever portion 313 moves in the opening section 3212, the first abutting portion 312 moves against the second abutting portion 322, and goes from the second valley 3224 to the second peak 3225 to let the rotating member 31 rotate radially and move axially at the same time due to the motion of the structure. Therefore, the purpose of ejecting the probe cover 4 is achieved. After the probe cover 4 is removed, the lever portion 313 is moved in the reverse direction so that the first abutting portion 312 returns to the initial position along the second abutting portion 322.

Figure 7:
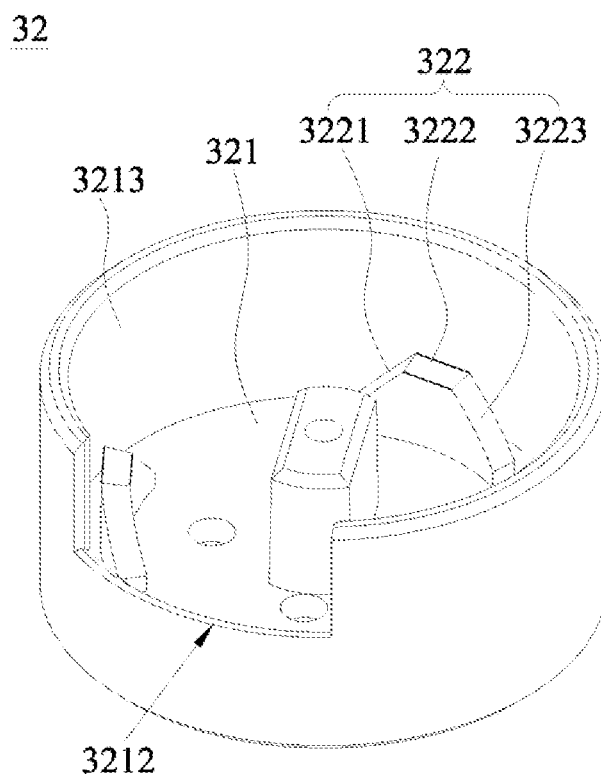
FIG. 7 is a schematic diagram of another embodied model of the socket according to the preferred embodiment of the present application.
Figure 8:
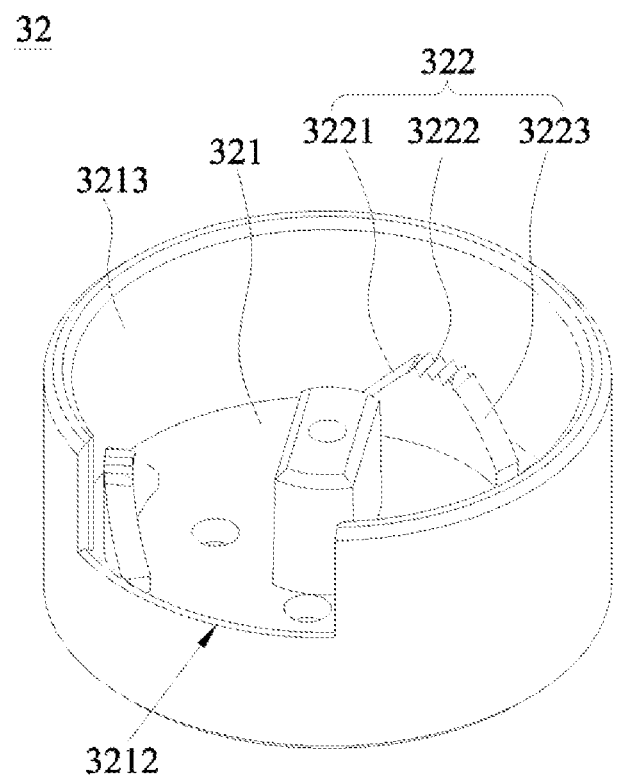
FIG. 8 is a schematic diagram of further another embodied model of the socket according to the preferred embodiment of the present application.

As shown in FIG. 7, an embodiment of the second abutting portion 322 may have an ascending slope 3221, a transversal surface 3222, and a descending slope 3223 that are sequentially connected to each other for the first abutting portion 312 to slide against them. When the lever portion 313 is forced to move in the opening section 3212, the first abutting portion 312 sequentially moves against the ascending slope 3221, the transversal surface 3222 and the descending slope 3223. That is, when the lever portion 313 is pulled to move in the opening section 3212, the first abutting portion 312 can sequentially move against the ascending slope 3221, the transversal surface 3222, and the descending slope 3223. When the first abutting portion 312 slides against the ascending slope 3221, the rotating member 31 rotates in the radial direction while the whole is axially displaced toward the socket 32 to gradually push the probe cover 4 away from the probe 30. When the first abutting portion 312 moves to the transversal surface 3222, the rotating member 31 continues to exert a pushing force to the probe cover 4. Afterward, when the first abutting portion 312 moves to the descending slope 3223, the rotating member 31 continues to rotate in the radial direction, further axially move toward a direction closed to the socket 32 and then returns back. Or, as shown in FIG. 8, in order to increase the pushing force applied by the rotating member 31 to the probe cover 4, a plurality of sawtooth-like grooves 3224 may be provided on the transversal surface 3222. Accordingly, when the first abutting portion 312 moves against the transversal surface 3222, the pushing force of the rotating member 31 relative to the probe cover 4 is enhanced by the structure of the said sawtooth-like grooves 3224.

Figure 9:
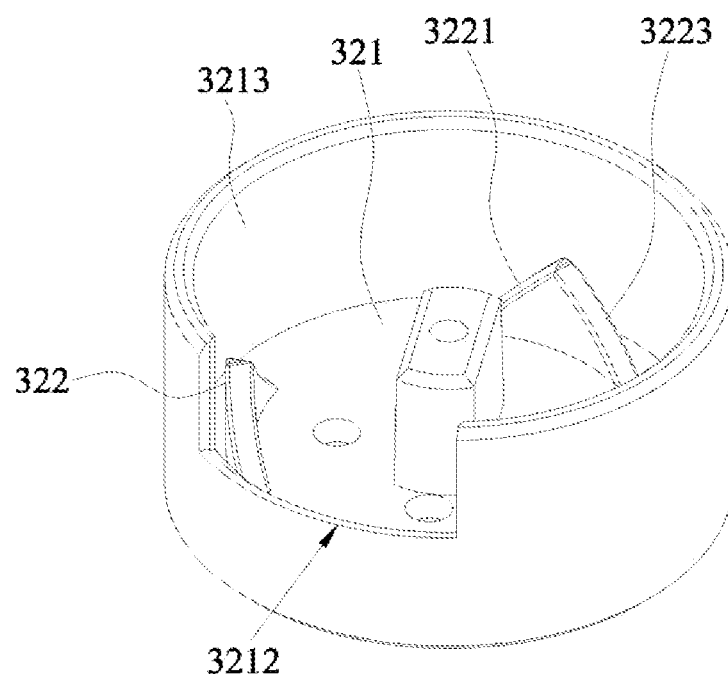
FIG. 9 is a schematic diagram of more another embodied model of the socket according to the preferred embodiment of the present application.

The second abutting portion 322 is not limited to the previous embodiment having the ascending slope 3221, the transversal surface 3222, and the descending slope 3223 that are connected to each other. Also, in another embodiment, as shown in FIG. 9, the second abutting portion 322 has a an ascending slope 3221 and a descending slope 3223 that are sequentially connected for the first abutting portion 312 to slide against them. When the lever portion 313 is pulled and moves in the opening section 3212, the first abutting portion 312 sequentially moves against the ascending slope 3221 and the descending slope 3223. Accordingly, when the lever portion 313 is pulled to move in the open section 3212, the rotating member 31 simultaneously rotates in the radial direction and is axially displaced in response to the abutment between the first abutting portion 312 and each of the ascending slope 3221 and the descending slope 3223. When the first abutting portion 312 abuts and moves along the ascending slope 3221, the rotating member 31 is axially displaced in a direction apart from the socket 32. When the first abutting portion 312 abuts and moves along the descending slope 3223, the rotating member 31 is axially displaced in a direction closed to the socket 32. When the second abutting portion 322 is formed as the above structure, the first abutting portion 312 can be designed as a bump for abutting against the second abutting portion 322, and hence, the structure of the second abutting portion 322 allows the rotating member 31 to rotate in the radial direction and shift in the axial direction.

If the ear thermometer 1 is provided with the spring 33, when the user pulls the lever portion 313 to displace it in the open section 3212, accordingly, the first abutting portion 312 abuts against and moves along the second abutting portion 322. If the second abutting portion 322 is an inclined surface, when the first abutting portion 312 moves to the second peak 3225, the spring 33 is compressed due to the motions of the radial rotation and axial displacement of the rotating member 31. When the lever portion 313 is free of pulling force, the rotating member 31 reacts to the elastic force of the spring 33 for reverse restoration to return back to the second valley 3224. If the second abutting portion 322 has the ascending slope 3221 and the descending slope 3223, similarly, when the first abutting portion 312 moves to the highest location of the ascending slope 3221, the spring 33 is compressed due to the motions of the radial rotation and axial displacement of the rotating member 31. Afterward, the first abutting portion 312 passes the ascending slope 3221 and starts to move to the descending slope 3223 when the user continues to pull the lever portion 313. Accordingly, the spring 33 is just free of the externally applied compression force and exerts an elastic force in a reverse direction. The rotating member 31 moves quickly and reliably along the descending slope 3223 due to the restored elastic force of the spring 33 so that the rotating member 31 moves toward the socket 32 and returns back. If the second abutting portion 322 has the ascending slope 3221, the transversal surface 3222, and the descending slope 3223, when the first abutting portion 312 continuously moves along the ascending slope 3223 to the transversal surface 3222, the spring 33 is compressed. Then, when the first abutting portion 312 is driven by the lever portion 313 and continues to move from the transversal surface 3222 to the descending slope 3223, the spring 33 is just free of the externally applied compression force and exerts an elastic force in a reverse direction. The rotating member 31 moves quickly and reliably along a reverse direction due to the elastic force of the spring 33 so that the rotating member 31 axially moves toward the socket 32 and returns back.

Figure 10:
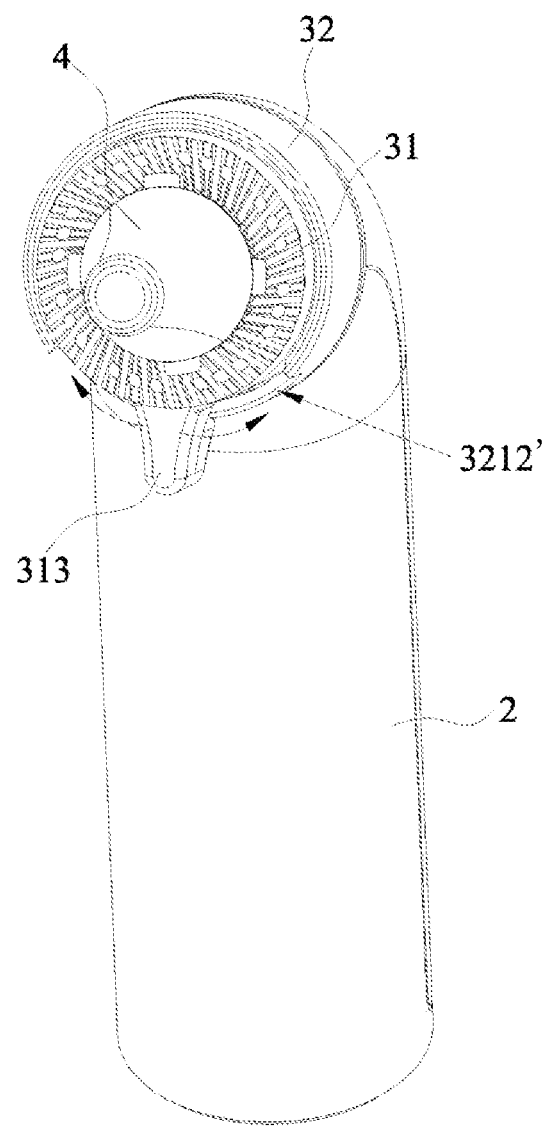
FIG. 10 is a schematic diagram of the ear thermometer according to the third embodied model according to the preferred embodiment of the present application.

Continuously referring to FIG. 10, this figure shows a schematic diagram of the third embodied model of the ear thermometer according to the preferred embodiment of the present application. In this embodiment, it can be seen that the open section 3212' is located below the measuring assembly 3. It needs to clarify here that the opening range of the opening section 3212' of the third embodiment is larger than that of the opening section 3212 mentioned above, and preferably has a double width. In this configuration, the user can pull the lever part 313 to the left or right according to personal practices to let the rotating member 31 have a clockwise or counterclockwise radial rotation. The probe cover 4 is ejected apart from the probe 30. When the lever portion 313 is forced to move to the right, the rotating member 31 acts in response to the coordinated motions of the first abutting portion 312 and the second abutting portion 322, and has a counterclockwise radial rotation and an axial displacement away from the socket 32. By contrast, when the lever portion 313 is forced to move to the left, the rotating member 31 acts in response to the coordinated motions of the first abutting portion 312 and the second abutting portion 322, and has a clockwise radial rotation and an axial displacement away from the socket 32. Of course, in this embodiment, the first abutting portion 312 and the second abutting portion 322 may be inclined surfaces respectively, or the second abutting portion 322 may have the ascending slope 3221 and the descending slope 3222, or have the ascending slope 3221, the transversal surface 3222, and the descending slope 3223 as various structural models. For detailed descriptions of specific operations, please refer back to the foregoing diagrams and text contents.

Figure 11:
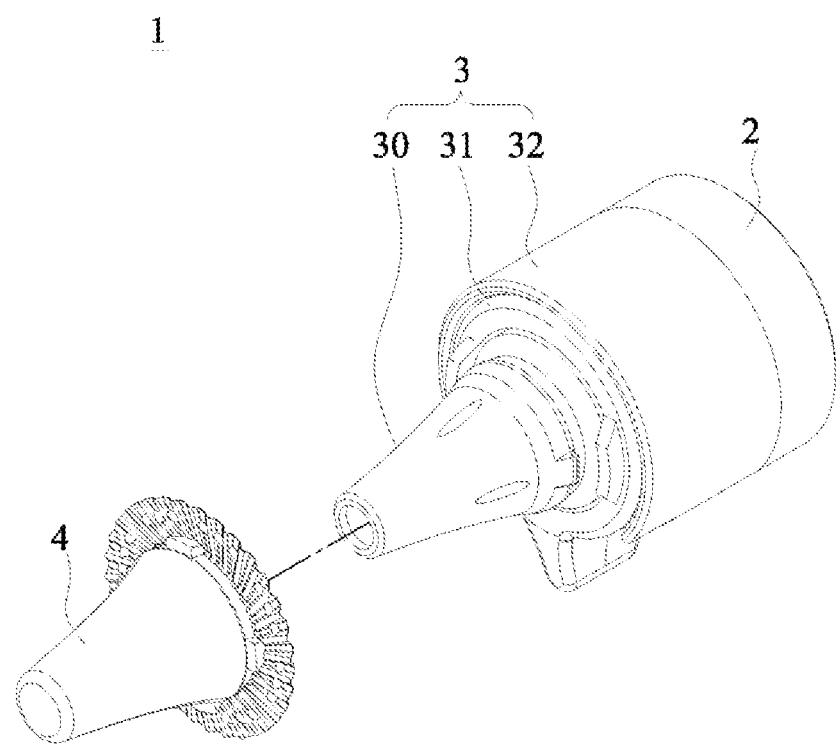
FIG. 11 is a schematic diagram of the ear thermometer according to the fourth embodied model according to the preferred embodiment of the present application.

Referring to FIG. 11, this figure shows a schematic diagram of the fourth embodied model of the ear thermometer according the preferred embodiment of the present application. In addition to the foregoing models of the ear thermometer 1 as shown in the various paragraphs and drawings, in order to meet the actual needs of current people and provide a more convenient infrared body temperature measurement product, the holding body 2 can also be formed as a small cylindrical structure integrated with the measuring assembly 3, and the overall volume of the ear thermometer 1 can be reduced. Consequently, the advantages are easy to carry and use it. In other embodiments, the foregoing small cylindrical structure has a wireless transmission mechanism that can be connected to external portable electronic apparatuses (such as mobile phones) to facilitate the user to control the temperature measurement or display the measurement result to the user.

In view of above, the ear thermometer with the probe cover ejection device proposed by the present application utilizes a special structure design so that the whole rotating member simultaneously rotate radially and move axially when the rotating member is motioned. The probe cover can be quickly and reliably ejected and removed from the probe by simultaneously exerting pushing forces along different directions on the probe cover. Through the second abutting portion on the circular bottom surface of the socket and the first abutting portion of the rotating member, the rotating member can simultaneously be radially rotated and axially displaced in response to an interactive motion between the first abutting portion and the second abutting portion after the lever portion is displaced by applied force. Accordingly, compared with a conventional ear thermometer, the area of the probe cover to which the force is applied can be extended from points to a surface so that the exact removal of the probe cover can be greatly improved and the integrity of the probe cover can be better maintained after removal to facilitate reuse. Furthermore, the present application integrates the lever part with the measuring assembly for the user to apply a force to the lever member for contacting the probe cover to eject it from the probe. When the user can push the lever portion, the pulling part moves together with the rotating member so that possible problems in the separated linkage structure can be avoided. The separated linkage structure is very easy to cause the deviation and uneven force due to the pivotal connection or pushing, and it cannot have an expected motion. That is, the probe cover cannot be removed reliably. However, in the present application, the lever portion is integrally formed in the radial direction of the rotating member so as to ensure the smooth motion of the whole and the reliability of removing the probe cover.

The foregoing embodiments of the invention have been presented for the purpose of illustration. Although the invention has been described by certain preceding examples, it is not to be construed as being limited by them. They are not intended to be exhaustive, or to limit the scope of the invention. Modifications, improvements and variations within the scope of the invention are possible in light of this disclosure.

What is claimed is:

1. An ear thermometer with a probe cover ejection device, comprising:
   a holding body; and
   a measuring assembly disposed at one end of the holding body, comprising:
      a probe;
      a rotating member including a ring cover with an opening formed in a middle of the ring cover, at least one first abutting portion axially extended from a lateral side of the ring cover, and a lever portion radially extended from the lateral side of the ring cover; and
      a socket including a circular bottom surface, a closed section and an open section defined on a periphery of the circular bottom surface, a side wall surface vertically provided on the closed section, an accommodating space sandwiched between the side wall surface and the circular bottom surface, and at least one second abutting portion formed on the circular bottom surface;
      wherein the rotating member is placed in the accommodating space and the first abutting portion is pressed against the second abutting portion to be in a relatively slidable state, the lever portion is protruded at a position of the open section of the socket, and the probe passes through the opening and one end of the probe is fixed to the circular bottom surface of the socket;
   wherein when the lever portion is displaced within the open section under force, the first abutting portion moves relative to the second abutting portion so that the rotating member whole and synchronously rotates radially and move axially to make a probe cover sheltered on the probe be radially and axially pushed and displaced simultaneously.

2. The ear thermometer with a probe cover ejection device according to claim 1, wherein the first abutting portion is an inclined surface and has a first valley and a first peak oppositely disposed so that the first abutting portion relatively abuts against the second abutting portion at a position that moves from the first valley to the first peak when the lever portion is displaced in the open section.

3. The ear thermometer with a probe cover ejection device according to claim 1, wherein the first abutting portion is a plane or a curved surface.

4. The ear thermometer with a probe cover ejection device according to claim 1, wherein the second abutting portion is an inclined surface and has a second valley and a second peak oppositely disposed so that the second abutting portion relatively abuts against the first abutting portion at a position the moves from the second valley to the second peak when the lever portion is displaced in the open section.

5. The ear thermometer with a probe cover ejection device according to claim 1, wherein the second abutting portion is a plane or a curved surface.

6. The ear thermometer with a probe cover ejection device according to claim 1, further comprising a spring, and a ring rib protruded from the opening of the ring cover, wherein one end of the spring abuts against the ring rib, and the other end of the spring abuts against a retaining surface of the probe.

7. The ear thermometer with a probe cover ejection device according to claim 6, wherein the other side of the ring cover opposite to the first abutting portion is axially extended to form a plurality of convexes.

8. The ear thermometer with a probe cover ejection device according to claim 7, wherein the number of the at least one second abutting portion is three, and the three second abutting portions are arranged equidistantly along a circumference of the circular bottom surface.

9. The ear thermometer with a probe cover ejection device according to claim 8, wherein the number of the at least one first abutting portion is three, and the three first abutting portions are respectively corresponding to and abutted against the three second abutting portions.

10. The ear thermometer with a probe cover ejection device according to claim 9, wherein the circular bottom surface of the socket has a pair of aligned protrusions, and one end of the probe has a pair of aligned grooves corresponding to the aligned protrusion so that the pair of the aligned protrusions are located in the aligned groove when the probe is fixed to the socket.

11. The ear thermometer with a probe cover ejection device according to claim 1, wherein the lever portion is clockwise or counterclockwise displaced within the open section so that the rotating member whole and synchronously rotate radially and move axially to eject the probe cover is ejected apart from the probe.

12. The ear thermometer with a probe cover ejection device according to claim 1, wherein the circular bottom surface is provided with a through hole for required electrical connecting devices to pass through.

13. The ear thermometer with a probe cover ejection device according to claim 1, wherein one end of the probe and the circular bottom surface are respectively provided with a plurality of screw holes, and the screw holes of the probe and the circular bottom surface are aligned with each other and fixed with screws.

14. The ear thermometer with a probe cover ejection device according to claim 1, wherein the second abutting portion has an ascending slope), a transversal surface, and a descending slope, and the first abutting portion sequentially moves against the ascending slope, the transversal surface and the descending slope.

15. The ear thermometer with a probe cover ejection device according to claim 14, wherein when the first abutting portion slides against the ascending slope, the rotating member rotates while the rotating member is axially displaced toward the socket to gradually push the probe cover away from the probe.

16. The ear thermometer with a probe cover ejection device according to claim 15, wherein a plurality of sawtooth-like grooves are provided on the transversal surface.

17. The ear thermometer with a probe cover ejection device according to claim 16, wherein when the first abutting portion moves to the transversal surface, the rotating member continues to exert a pushing force to the probe cover.

18. The ear thermometer with a probe cover ejection device according to claim 1, wherein the second abutting portion has an ascending slope and a descending slope, and the first abutting portion sequentially moves against the ascending slope and the descending slope.

19. The ear thermometer with a probe cover ejection device according to claim 18, wherein when the first abutting portion slides against the ascending slope, the rotating member rotates while the rotating member is axially displaced toward the socket to gradually push the probe cover away from the probe.

20. The ear thermometer with a probe cover ejection device according to claim 1, wherein the first abutting portion can be designed as a bump for abutting against the second abutting portion.

* * * * *